United States Patent [19]

Loi

[11] Patent Number: 4,701,230
[45] Date of Patent: Oct. 20, 1987

[54] METHOD FOR MANUFACTURING A BREAST PROSTHESIS

[75] Inventor: Chay H. Loi, Monterey Park, Calif.

[73] Assignee: Nearly Me, Los Angeles, Calif.

[21] Appl. No.: 757,135

[22] Filed: Jul. 18, 1985

[51] Int. Cl.$^4$ .............................................. A61F 2/50
[52] U.S. Cl. .................... 156/145; 156/156;
156/245; 156/292; 156/308.4; 623/7
[58] Field of Search .............. 156/145, 156, 245, 292,
156/308.4; 623/7

[56] References Cited

U.S. PATENT DOCUMENTS

| | | | |
|---|---|---|---|
| 3,795,921 | 3/1974 | Zucker | 623/7 |
| 3,852,833 | 12/1974 | Köneke et al. | 623/7 |
| 4,125,117 | 11/1978 | Lee | 623/7 X |
| 4,199,825 | 4/1980 | Knoche | 623/7 |
| 4,247,351 | 1/1981 | Rechenberg | 623/7 X |
| 4,249,975 | 2/1981 | Rechenberg | 623/7 X |
| 4,401,492 | 8/1983 | Pfrommer | 156/145 X |

*Primary Examiner*—Robert A. Dawson
*Attorney, Agent, or Firm*—Herzig & Yanny

[57] ABSTRACT

A method for fabricating breast prostheses in accordance with the invention includes the steps of forming an outer sheet to a concave configuration; forming an inner sheet to a concave configuration; bonding an intermediate sheet to a form member having a concave inner surface and a convex outer surface; sealing the inner sheet, intermediate sheet, and outer sheet together along their peripheries, thereby forming an outer chamber defined by the outer sheet and the intermediate sheet and an inner chamber defined by the intermediate sheet and the inner sheet, the inner chamber containing the form member; filling the outer chamber with uncured silicone gel; compressing the chamber to remove the air therefrom; placing the compressed chamber in a vacuum chamber to further remove any remaining air therefrom; sealing the chamber; and curing the liquid silicone into a gel.

1 Claim, 13 Drawing Figures

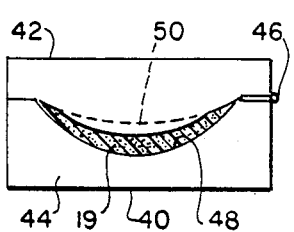
FIG. 4.
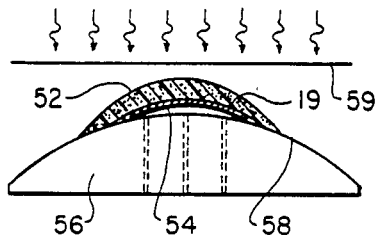
FIG. 5.
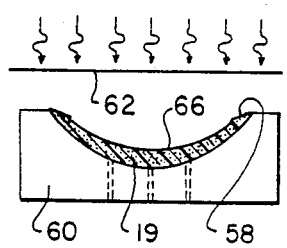
FIG. 6.
FIG. 8.
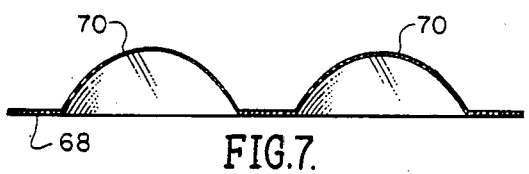
FIG. 7.
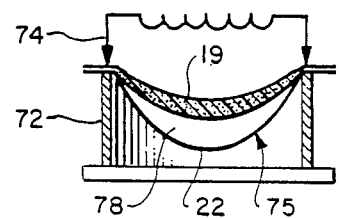
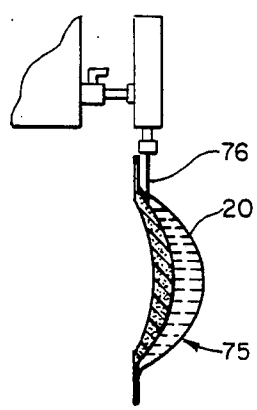
FIG. 9.
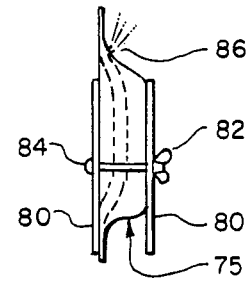
FIG. 10.
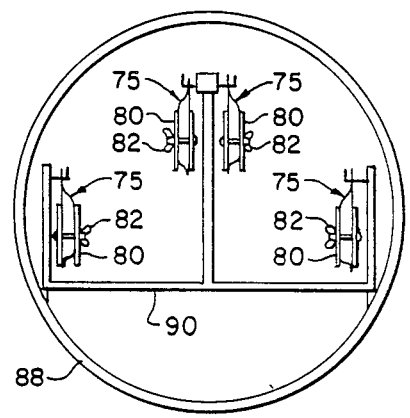
FIG. 11.
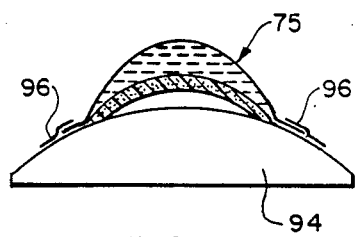
FIG. 12.
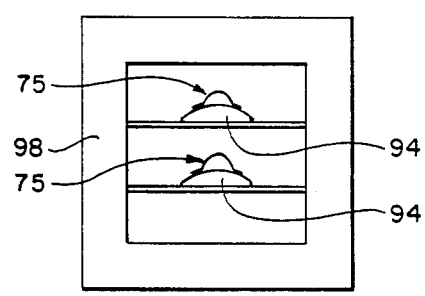
FIG. 13.

METHOD FOR MANUFACTURING A BREAST PROSTHESIS

BACKGROUND OF THE INVENTION

1. Field of the Invention

The field of the invention is that of human body prosthetics and more particularly a breast prosthesis and method of fabrication therefor.

2. Description of the Prior Art

It is conventional practice following post mastectomy surgery to have the patient fitted with a breast prosthesis to augment that portion of the pectoral area which has been removed. The selection and purchase of such a prosthesis is much more complicated than that of almost any other body part.

There has been an apparent lack of awareness of the problem that exists today in the wearing of breast prostheses by women who have had a mastectomy. Prostheses that are presently on the market are made for either side of the body and emphasize the cosmetic aspect. However, there is an apparent unawareness by manufacturers that when a breast is removed it is not a totally cosmetic problem. When a breast is removed, the corresponding entire side of the physical anatomy goes into a distortion, that is, a misalignment of the entire skeletal system from the shoulders to the cervical area. In many instances, the results of removal and misalignment are felt in the lower lumbar area. To the best of the applicant's knowledge, prior art prostheses do nothing to compensate for this anatomical misalignment. They neither support the arm nor realign the shoulder in order to keep both the shoulder and the cervical area in their original confirmation. Further, they do little to give the apppearance, the confidence and the social acceptability that is so drastically required after these women have gone through this traumatic experience. Women wearing the prior art prostheses are constantly aware of the appliance being worn, because it does not stay in place, does not fill out their garments and does not look like their real breast. The prosthesis may become a source of aggravation and embarrassment. These women are always looking for a breast substitute that will give them comfort and confidence. Typically, they have bought many appliances, each time hoping that this one appliance would give them the confidence and comfort they desire, but finally finding that their new prosthesis is of little or no improvement over their prior purchase.

Breast prosthesis devices typically are neither sculptured nor contoured to actually resemble, function in movement, or fit, as a human breast, but are flat on the inner side and thus not shaped to conform to the post-operative chest and body contour of the wearer. Also, the known prior art is subject to many other well-defined deficiencies including the following:

They are not sized according to bust size nor in accordance with torso measurements. They are not separably designed as left and right breasts. They are neither shaped nor contoured on the underside or underpart to match the contours of an actual breast. Some of the materials used are too heavy for wearing comfort. Some deflate or deteriorate with usage. Some must be sewn into special expensive bras. Most do not conform to the body in its anatomical state or contour after a radical mastectomy. They lack the flexibility and texture of flesh, both statically and dynamically. They do not accommodate various body sizes, that is, girth dimensions; nor do they offer various cup sizes. They accommodate to the frontal breast only, not the abnormal chest contour existing following the mastectomy. Typically, they have a flat, not contoured backing, and are hemispherical in design, rather than being shaped to provide for changes in shape comfortable to body movements. Often, special brassieres are required causing great inconvenience and cost. The weight distribution is neither proper nor optimum, which contributes to discomfort, fatigue and poor posture. The feeling against the body is false or unreal. They do not possess the desired degree of flexibility and texture, not having the capability of moving with the body during physical activity in such a way as to simulate or duplicate the characteristics of a natural breast. In use, they give gaps or visible delineations under tight fitting outer garments, especially those made of delicate fabrics. Many harden after washing, are irritable to the skin, or feel unnatural or uncomfortable. In some devices, for example, an adhesive is used to retain the device in position on the wearer as in the device in the U.S. Pat. No. 4,125,117. In other instances, the use of air filling is employed in order to attempt to effect the natural contouring, as in U.S. Pat. No. 3,852,833. Such devices, however, have undesirable side effects as, for example, the discomfort of using an adhesive or a suction mechanism to maintain interface of the prosthesis with the body of the user and the unavoidable "bowing" effect introduced by the use of air filling which naturally forms a spherical shape as opposed to the natural contours of the body of the wearer.

Contrarily, the herein invention possesses all of the desirable qualities and characteristics set forth in detail hereinafter, and overcomes the above deficiencies of the prior art.

SUMMARY OF THE INVENTION

The invention provides a breast prosthesis comprising a form member having a convex and a concave surface. Positioned adjacent to the concave surface of the form member is an inner skin sheet; and positioned adjacent to the convex surface of the form member is an intermediate skin sheet. Both the inner and intermediate skin sheets are sealingly attached to one another at their peripheries, thereby sealing the form member between these two sheets. An exterior skin sheet corresponding to a human breast in desired shape and appearance is positioned adjacent the intermediate skin sheet and is sealingly attached to the periphery of the inner skin sheet, thereby forming a cavity defined by the intermediate skin sheet and the outer skin sheet. A fluid, such as silicone gel, is disposed within the cavity defined by the outer and the intermediate skin sheets.

The invention also provides a method for fabricating a breast prosthesis including the steps of: providing a form member having a convex and a concave surface; shaping an intermediate skin sheet of thin, flexible material and molding the intermediate skin sheet upon the convex surface of the form member, whereby the intermediate skin sheet adheres to the convex surface of the form member; shaping an outer skin of thin, flexible material on a mold of parti-cylindrical configuration corresponding to human breast and having the desired exterior shape and appearance of the prosthesis; positioning the intermediate skin sheet and form member combination within the outer skin sheet; shaping and positioning an inner skin sheet of thin flexible material into intimate contact with the concave surface of the form member; sealing the inner skin sheet, the form member and intermediate skin sheet combination, and the outer skin sheets together about the peripheries thereof, thereby forming a combination having a cavity defined by the intermediate skin sheet and the outer skin sheet; filling the cavity with a liquid through a passage in the outer skin sheet; removing any air trapped within the cavity and sealing the passage; and, curing the liquid into a gel.

BRIEF DESCRIPTION OF THE DRAWINGS

In order to facilitate understanding of the present invention, reference will now be made to the appended drawings of a preferred specific embodiment of the present invention. Such drawings should not be construed as limiting the invention which is properly set forth in the appended claims.

FIGS. 4, 5, 6, 7, 8, 9, 10, 11, 12 and 13 are diagrammatic illustrations depicting the process of fabricating the prosthesis.

DETAILED DESCRIPTION OF A PREFERRED EMBODIMENT

Referring to the figures of drawings wherein like numbers of reference designate like elements throughout, a preferred embodiment of a prosthesis made in accordance with the present invention is hereinafter described.

Figure 2:
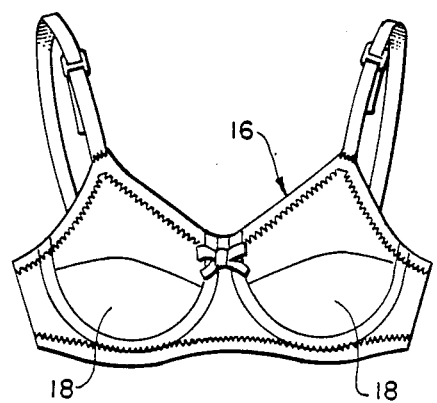
FIG. 2 is a front view of the brassiere with the prosthesis inserted in one cup of the garment.
Figure 1:
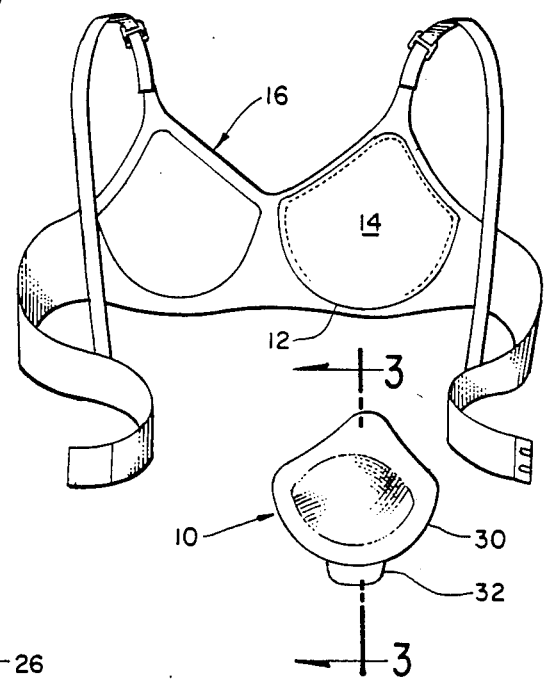
FIG. 1 is a rear view of a brassiere showing the pocket into which the prosthesis is inserted.

As shown in FIGS. 1 and 2, a woman who has undergone a mastectomy may wear a brassiere 16 which will hold and support a prosthesis 10 to simulate the appearance of the missing breast. The prosthesis 10 is inserted through an unattached opening 12 of a pocket flap 14 sewn on the back side of brassiere 16.

A hem 30 and a tab 32, as seen in FIG. 1, may also be used in sewing the prosthesis 10 to insure that the prosthesis, once sewn into pocket 14, will not shift with movement of the wearer.

The breast prosthesis 10 is manufactured in various sizes relating to the size designation of integral cups 18 comprising a brassiere 16 as best shown in FIG. 2. The prosthesis is shaped generally in the configuration of the left or right mammillary glands as required by a patient having experienced mastectomy surgery.

Figure 3:
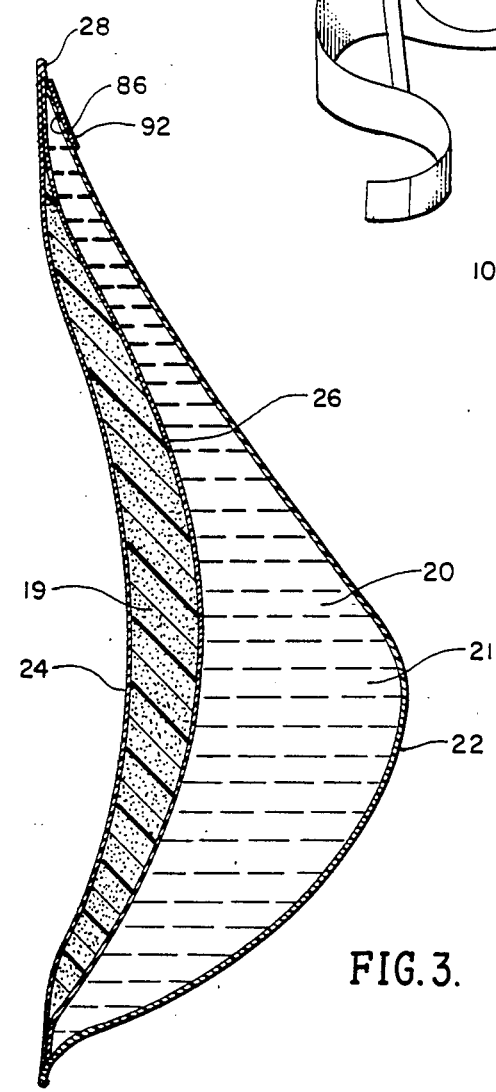
FIG. 3 is a sectional view of the breast prosthesis taken along line 3—3 of FIG. 1 with the cover removed.

As best seen in FIG. 3, the prosthesis 10 comprises an outer and front sheet or skin 22, an intermediate or middle sheet or skin 26, and an inner or rear sheet or skin 24. The sheets are sealed together at their peripheries 28 and form a sealed compartment 21 between intermediate sheet 26 and outer sheet 22.

A foam member 19, described in further detail below, is disposed between intermediate sheet 26 and inner sheet 24 and is bonded to sheets 26 and 24. A fluid 20, also described in further detail below, is disposed in compartment 21.

A detailed description of the process employed to fabricate the prosthesis 10, as illustrated in FIGS. 1 and 3, will be hereinafter explained and are diagrammatically illustrated in FIGS. 4 through 13.

FIG. 4 illustrates the initial operation of fabricating form foundation 19, as shown in FIG. 3. Mold box 40 is comprised of a top convex mold section 42 and a bottom concave mold section 44 hinged at 46. The hollow cavity 48 within the closed mold box 40 is shaped to the configuration requirements of the finished product.

The contacting surfaces of the mating mold, sections 42 and 44, are formed with a curved radius 50 of either 12, 14, or 16 inches, corresponding to the chest circumferences of varying body sizes. Mold box 40 is heated to a temperature of about 80-100 degrees Farhenheit and a precise mixture of setting compound and polyurethane foam is poured into a cavity 48 where it expands to the confining shape of hollow cavity 48. The foam foundation 19 thus formed is removed and placed on a drying rack for a period of about 15 hours.

If desired, mold section 42 may be heated prior to the pouring of the foam material so that the resultant product will have greater porosity at its area of contact with the mold section 42 than it does at the area of its contact with mold section 44.

While any suitable foam material can be employed, it is presently preferred to employ a supersoft, Freon-blown polyurethane foam of low density (in the range of 2-4 lb./cubic foot) with a partially open, partially closed cell structure. While other materials having a tissue-like resiliency may be used, for example, various gels, a foam is preferred because it may provide the desired degree of dimensional stability, while adding very little weight. Thus, it is the combination of vertical dimensional stability with a horizontal contour-adapting flexibility which is preferred in the present invention.

As stated, mold section 42 may be heated, causing the foam to be more porous along the surface thereof which will contact middle skin 26, and more dense along the surface which will contact back skin 24. If this is done, foam foundation 19 will more closely simulate natural breast tissue in "feel," weight, and action.

When mold section 42 and 44 are separated, foam foundation 19 may be removed therefrom. If desired, the rear or back skin 24 may be adhesively bonded to that portion of the foam which was formed adjacent to mold section 44. This has been found to be particularly useful in the larger prostheses and sometimes helpful in smaller ones. During certain actions of the wearer, pressure on the front of the prosthesis may cause air to be driven from within the foam foundation 19 toward the rear of prosthesis 10. If back skin 24 is not bonded to the rear surface of the foam foundation, the air may cause a bubble to form between the foam and the skin which might, in some instances, be slightly uncomfortable to the wearer. Accordingly, if the back skin is bonded to the foam, such discomfort cannot occur because no bubbling can take place.

FIG. 5 illustrates a method for adhering a sheet or film to the convex surface 52 of foam foundation 19. Cured foundation 19 is coated with an adhesive cement on its convex surface 52; fitted onto a mold sizing insert 54; and mounted on a hollow convex form 56. The radius 58 of convex form 56 corresponds to the curved radius 50 of mold box 40. Form 56 with foundation 19, is placed within a vacuum forming machine, wherein a sheet 59 of any suitable material may be positioned within a standard heating frame (not shown) and heated by any suitable means. When the sheet has been heated to a predetermined temperature, it can be lowered over form 56 so that it can be vacuum formed against convex surface 52 of foundation 19 thus forming intermediary skin 26 as shown in FIG. 3.

Although sheet 59 may be of any suitable material, it has been found that the polyurethane film commercially known as "tuftane" is very satisfactory since its texture and touch quality closely simulate human skin. Further, the material is quite strong and is resistant to hydrolysis and fungicidal attack. Although this material is presently deemed preferable, those skilled in the art will realize that a wide variety of other films may be employed to achieve the desired results.

Sheet 59 is, in a preferred embodiment, about 0.004 inches in thickness.

At this stage of fabrication, referring now to FIG. 6, foundation 19 is inserted in a hollow mold 60 in the vacuum forming machine, wherein a heated polyurethane film 62 about 0.004 inches thick is drawn onto the inner surface 66 of foundation 19 which is cemented as by liquid polyurethane, thus forming inner skin 24 (FIG. 3).

The illustration in FIG. 7 depicts a sheet 68 of about 0.006 inches in thickness which has been heated and molded in the vacuum forming machine to produce a multiple number of sized cup-shaped contours 70 which, in the final assembly, form outer skin 22 of prosthesis 10.

FIG. 8 shows composite elements 19, 22, 24 and 26 placed into a parti-cylindrical form 72 shaped to the configuration of prosthesis 10 and therein fused together by means of a welding device 74 to form a leak-proof pouch assembly 75.

Referring now to FIG. 9, fused assembly 75 of the aforementioned composite elements is injected with a silicone gel compound 20 comprised of a viscous mixture of compounds A (hardener) and, B (resin) by means of a needle 76 which is inserted into the top-most portion of the empty cavity 78 defined by outer skin 22 and intermediate skin 26 for exclusion of air.

Air trapped in chamber 78 is removed by compressing assembly 75 between two flat plastic plates 80 (FIG. 10) by means of winged nut 82 on screw 84. The air is released through hole 86 produced by needle 76.

Referring to FIG. 11, the remainder of air in cavity 78 is evacuated in a vacuum chamber 88, wherein multiple assemblies 75 are hung on a rack 90 and sealed within the vacuum chamber for a period of approximately 60 minutes. Upon removal of each assembly 75 from vacuum chamber 88, a sealing patch 92 (see FIG. 3) is cemented over needle hole 86.

Referring to FIG. 12, the assemblies are now attached to a radius form 94 by means of mastic tape 96 binding the edges to said form 94. The loaded radius form 94 is then placed in an electric oven 98 (see FIG. 13) wherein the silicone gel in assemblies 75 are cured at a temperature of about 125°–135° F. for a period of approximately 15 hours. Each of several radius forms 94 placed in oven 98 has sufficient length to accommodate thereon a plurality of assemblies 75, thereby providing a cure of several assemblies 75 for each oven cure.

The final operation consists of trimming the excess film from the peripheral edges of the cured assemblies, thus producing the completed prosthesis device 10.

Those skilled in the art will quickly realize that a prosthesis formed in accordance with the method of the present invention, or employing the structure of the present invention, may utilize a wide variety of materials and may be formed in a wide variety of methods. In any event, the materials, structure, and methods, though perhaps not resembling the exemplary embodiment described here, will nevertheless employ the present invention as defined in the following claims.

I claim:

1. A method of forming a prosthesis comprising the steps of:
   providing a foam member having a convex and a concave surface;
   shaping an intermediate skin sheet of thin, flexible material and molding the intermediate skin sheet upon the convex surface of the foam member whereby the intermediate skin sheet adheres to the convex surface of the foam member;
   shaping an outer skin sheet of thin, flexible material on a mold of parti-cylindrical configuration corresponding to a human breast and having the desired exterior shape and appearance of the prosthesis;
   positioning the intermediate skin sheet and foam member combination within the outer skin sheet;
   shaping and positioning an inner skin sheet of thin flexible material in intimate contact with the concave surface of the foam member;
   sealing with the inner skin sheet, the foam member and intermediate skin sheet combination and the outer skin sheet together about the peripheries thereof, thereby forming a combination having a cavity defined by the intermediate skin sheet and the outer skin sheet;
   filling the cavity with a liquid through a passage in the outer skin sheet;
   removing any air trapped within the cavity;
   sealing the passage;
   curing the liquid into a gel;
   providing a mold for said foam member, and pouring and curing a foam material into the mold; and
   wherein the step of providing a foam member further includes the step of heating the mold prior to the pouring step, thereby causing that portion of the foam member adjacent to the mold to have greater porosity than the remainder thereof and less density.

* * * * *